United States Patent [19]

Drake

[11] Patent Number: 4,529,827

[45] Date of Patent: Jul. 16, 1985

[54] DEHYDRATION OF ALCOHOLS

[76] Inventor: Charles A. Drake, c/o French, Hughes and Doescher, P.O. Box 2443, Bartlesville, Okla. 74005

[21] Appl. No.: 604,714

[22] Filed: Apr. 27, 1984

[51] Int. Cl.³ .............................................. C07C 1/24
[52] U.S. Cl. .................................... 585/640; 502/355
[58] Field of Search ................. 585/639, 640; 502/355

[56] References Cited

U.S. PATENT DOCUMENTS

| | | | |
|---|---|---|---|
| 2,636,057 | 4/1953 | Cutcher et al. | 585/640 |
| 2,671,121 | 3/1954 | Banes et al. | 260/682 |
| 2,919,973 | 1/1960 | Stillwell et al. | 585/639 |
| 3,197,417 | 7/1965 | Folkins et al. | 252/442 |
| 3,360,585 | 12/1967 | Winnick | 260/681 |
| 3,391,214 | 7/1968 | Fetterly | 260/681 |
| 3,595,929 | 7/1971 | Lakodey et al. | 260/666 |
| 3,665,048 | 5/1972 | Grane et al. | 585/640 |
| 3,880,776 | 4/1975 | Box, Jr. et al. | 252/466 PT |
| 3,979,504 | 9/1976 | Ziegenhain et al. | 502/355 |
| 4,006,198 | 2/1979 | Tesei et al. | 585/640 |
| 4,144,277 | 3/1979 | Walker et al. | 260/666 A |
| 4,147,736 | 4/1979 | Cokhberg et al. | 585/640 |
| 4,234,752 | 11/1980 | Wu et al. | 585/640 |
| 4,320,074 | 3/1982 | Birchall et al. | 423/630 |
| 4,398,051 | 8/1983 | Araki et al. | 585/640 |

OTHER PUBLICATIONS

"The Removal of Excess Fluoride from Drinking Water by Activated Alumina", *American Water Works Association Journal*, Jan. 1979, p. 45.

"Alumina Properties, Technical Paper No. 10", *Alcoa Research Lab.*, 1960, pp. 46, 52 and 53.

*Primary Examiner*—D. E. Gantz
*Assistant Examiner*—Anthony McFarlane

[57] ABSTRACT

An improved process for dehydrating alcohols in which the alumina used in the dehydration process is heat treated to produce essentially pure chi-alumina.

5 Claims, No Drawings

DEHYDRATION OF ALCOHOLS

This invention relates to the dehydration of alcohols. It further relates to a process for the dehydration of alcohols. In particular it relates to a pretreatment of an alumina catalyst used in the dehydration of alcohols.

BACKGROUND

The dehydration of alcohols to produce olefins is known. This process is important because the olefins produced from the dehydration are used in further processes. For example, 2-alkyl-1-alkenes such as 2-methyl-1-butene and 4-methyl-1-pentene are well known polyolefin modifiers and there is a large market for these compounds.

Principally the dehydration reaction is one involving the removal of the elements of water from the alcohol. In some cases a single olefin will result upon the dehydration; in others a mixture of olefins will be obtained. For instance, the dehydration of 2-methyl-2-butanol can produce at least two olefins, 2-methyl-1-butene, which as mentioned before is a desirable product, and 2-methyl-2-butene, a less desirable product. The formation of other products occurs through isomerization.

It is the object of this invention to maximize the production of desired olefin products, while minimizing the production of undesirable olefin products through isomerization.

It is a general object of this invention to dehydrate an alcohol. It is a further object of this invention to provide a process for the dehydration of alcohols. A specific object of this invention is to provide a pretreatment of the alumina catalyst used in the dehydration of alcohols that increase the selectivity and conversion rate of the alcohol, minimizing the isomerization of the olefin. Other objects will become apparent from the following disclosure.

SUMMARY OF THE INVENTION

According to the present invention, the alumina catalyst used in the dehydration of alcohols is subjected to a heat pretreatment whereby the catalyst is subjected to temperatures of at least about 450° C. for a sufficient time in the presence of a flowing inert gas. The thus pretreated catalyst gives higher conversion and selectivity at the reaction temperatures where untreated catalysts give little or no reaction.

In a preferred embodiment, the alumina catalyst is subjected to a heat pretreatment whereby the catalyst is subjected to temperatures of about 550° C. for about three hours in a flowing nitrogen atmosphere.

DETAILED DESCRIPTION OF THE INVENTION

The alumina catalyst used in the preferred embodiment of the present invention is a mixed boehmite (aluminum oxide-hydroxide)/chi-alumina composition. The heat treatment temperature can range from about 450° C. to about 650° C., but preferably the temperature will be at about 550° C. The treatment should last from about 1 hour to about 10 hours, but preferably for about 3 hours. The heat treatment should occur in the presence of a gas that is inert with the alumina. The preferred gas is nitrogen. The treated alumina is then allowed to cool. A relatively pure chi-alumina catalyst results from this treatment. This chi-alumina catalyst results in greater conversion percentage and a higher yield percentage in dehydrating alcohols than mixed compositions.

The heat treatment can be accomplished in any conventional manner. The alumina catalyst can be treated either within the reactor used in the dehydration of the alcohol or in a separate vessel and then transferred to the reactor.

Alcohols which are dehydrated to the corresponding olefins by means of this invention generally include the straight chain or branched-chain alcohols containing from 2 to about 20 carbon atoms per molecule. These can contain primary, secondary, or tertiary alcohol groups. This invention yields especially beneficial results with branched-chain alcohols containing from 4 to about 10 carbon atoms.

Alcohols which can be used in the process of this invention include ethanol, 1-propanol, 2-methyl-2-propanol, 2-methyl-1-butanol, 3-methyl-1-butanol, 3-methyl-2-butanol, 2,4-dimethyl-1-hexanol, 1-octanol, 2,11-dimethyl-2-dodecanol, 1-hexadecanol, 1-eicosanol, and the like.

Olefins produced by the process of this invention generally correspond to the starting alcohol from which elements of water have been removed. For example, the dehydration of 2-methyl-1-butanol will result, generally, in 2-methyl-1-butene. This invention minimizes isomerization which in this example would produce 2-methyl-2-butene and the like.

The inert carrier gas employed in this invention can be any gas, or any inert gas, which is unreactive at existing reaction conditions, such as nitrogen, helium, argon, and the like, or mixtures thereof.

It is preferable to employ the desirable alcohol and inert carrier gas in the absence of any additional solvent or diluent. It is within the scope of this invention to employ any solvent in the dehydration reaction which will not adversely affect the reaction.

The alcohol generally is added to the reactor under desired reaction conditions at a rate of from about 0.1 to 20 weight hourly space velocity, and preferably 0.5 to 2 weight hourly space velocity.

The flow of inert carrier gas has not been found to be critical in obtaining good results according to this invention. In general, the flow rate can vary from about 3 liters per hour to about 66 liters per hour, however, an optimum rate of conversion and selectivity occur between 40 liters per hour and 50 liters per hour.

Generally, temperatures in the range of from about 200° to 550° C. are suitable for the desired dehydration reaction to occur. It is currently preferable, however, to employ temperatures in the range of 300°–450° C. Due to the exothermicity of the dehydration reaction, it may be desirable to provide external means of cooling for the desired temperature control.

The pressures under which the desired dehydration reaction will occur can vary widely, for example, from about 50 to about 3,500 kPa. It is generally preferable, however, to maintain some pressure and pressures in the range of 100–700 kPa are now contemplated as being desirable.

The reaction mixture can be separated readily into desired products, by-products, and unreacted starting materials using conventional methods such as solvent extraction, fractional distillation, fractional condensation, etc. An especially suitable means for isolating desired product involves the passage of gaseous reactor effluent into successively cooler zones, for example, 50° C. followed by 0° C. followed by −70° C. Most of the water and unreacted starting materials condense at the higher temperatures, while desired olefins are recovered at the lower temperatures.

EXAMPLE I

In this control run 2-methyl-1-butanol was subjected to a dehydration reaction utilizing alumina not pretreated according to this invention. The alumina was designated F-1 and was obtained from Aluminum Company of America. A ½"×20" stainless steel tubular reactor was charged with 38 g of the alumina (12–20 mesh U.S. standard size) and heated up to reaction temperature under nitrogen flowing at a rate of about 1 SCFH. The alcohol was then fed to the reaction zone at a rate of 36 mL/hr. Effluent from the reaction zone was collected and analyzed by gas chromatography.

The results obtained in this run are presented in Table I below.

TABLE I

| Run No. | Temp. °C. | Feed Conversion, % | Selectivity to 2-MB-1[a], % |
|---|---|---|---|
| 1 | 340 | very low[b] | — |
| 2 | 360 | 72 | 82 |

[a] 2-MB-1 = 2-methyl-1-butene
[b] less than 10% conversion

The results show the untreated catalyst gives low conversion at 340° C. but moderate conversion of feed and selectivity to 2-methyl-1-butene product at 360° C.

F-1 alumina is characterized by following typical properties:

| Composition- | $Al_2O_3$ | 92.0 wt. % |
|---|---|---|
|  | $Na_2O$ | 0.90 wt. % |
|  | $Fe_2O_3$ | 0.08 wt. % |
|  | $SiO_2$ | 0.09 wt. % |
| Loss on Ignition (1100° C.)- |  | 6.5 wt. % |
| Form- | Granular |  |
| Surface Area- | 210 m²/g |  |

EXAMPLE II

In this inventive run the F-1 alumina was subjected to a pretreatment involving heating about 100 g of the alumina to 550° C. for 3 hours in flowing nitrogen at a rate of 1 SCFH. After cooling to ambient temperature, 38 g of the alumina was charged to the tubular reactor used in Example I. The 2-methyl-1-butanol feed was introduced into the heated reaction zone at a rate of 36 mL/hr while nitrogen was maintained at 44.3 L/hr. Reactor effluent was analyzed as in Example I. The results are presented in Table II below.

TABLE II

| Run No. | Temp. °C. | Feed Conversion, % | Selectivity to 2-MB-1[a], % |
|---|---|---|---|
| 1 | 340 | 89 | 90 |
| 2 | 360 | 100 | 65 |

The results show that heat treating of the F-1 alumina according to this invention gave a catalyst with high activity and selectivity under conditions wherein the untreated catalyst was only slightly active.

The F-1 alumina was also examined by x-ray diffraction and surface area measurements before and after the inventive heat pretreatment. These tests showed that the surface area decreased from 232 m²/g to 142 m²/g. However, the x-ray analysis showed that the alumina changed from a mixed boehmite (aluminum oxide-hydroxide)/chi-alumina composition) to a relatively pure chi-alumina form.

I claim:

1. A process for dehydrating an alcohol to an olefin comprising subjecting said alcohol under dehydration reaction conditions of temperature and pressure to the presence of a chi-alumina catalyst formed by heat treating a mixed boehmite/chi-alumina to a temperature from about 450° C. to about 650° C. in the presence of an inert gas for a period ranging from about 1 to about 10 hours.

2. A process according to claim 1 where said heat treating temperature is 550° C.

3. A process according to claim 1 where said heat treating lasts about 3 hours.

4. A process as in claim 1 where said alcohol is 2-methyl-1-butanol.

5. A process as in claim 1 where said inert gas is nitrogen.

* * * * *